(12) United States Patent
Lee et al.

(10) Patent No.: US 7,118,923 B2
(45) Date of Patent: Oct. 10, 2006

(54) NANOPOROUS MEMBRANE IMMUNOSENSOR

(75) Inventors: Gil U. Lee, West Lafayette, IN (US); Carolyn Yanavich, Alexandria, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 10/734,241

(22) Filed: Dec. 15, 2003

(65) Prior Publication Data

US 2004/0126899 A1    Jul. 1, 2004

Related U.S. Application Data

(62) Division of application No. 09/614,727, filed on Jul. 12, 2001, now Pat. No. 6,676,904.

(51) Int. Cl.
*G01N 33/543* (2006.01)

(52) U.S. Cl. ............... 436/518; 436/524; 436/164; 436/172; 435/6; 435/7.1; 435/287.1; 435/422; 435/101

(58) Field of Classification Search ............ 435/6, 435/7.1, 287.1; 436/518, 524, 526, 164, 436/172; 422/57, 58, 101; 210/600, 321.75, 210/348
See application file for complete search history.

(56) References Cited

U.S. PATENT DOCUMENTS

| | | | |
|---|---|---|---|
| 4,493,815 A | 1/1985 | Fernwood et al. | |
| 4,632,901 A | 12/1986 | Valkirs et al. | |
| 4,777,021 A | 10/1988 | Wertz et al. | |
| 4,797,259 A | 1/1989 | Matkovich et al. | |
| 5,100,626 A | 3/1992 | Levin et al. | |
| 5,137,634 A | 8/1992 | Butler et al. | |
| 5,137,804 A | 8/1992 | Greene et al. | |
| 5,830,680 A * | 11/1998 | Meyerhoff et al. | 435/7.92 |
| 5,843,767 A | 12/1998 | Beattie et al. | |
| 6,051,380 A * | 4/2000 | Sosnowski et al. | 435/6 |
| 6,180,418 B1 | 1/2001 | Lee et al. | |
| 6,225,131 B1 * | 5/2001 | van Damme et al. | 436/524 |
| 6,303,389 B1 | 10/2001 | Levin et al. | |
| 6,352,862 B1 | 3/2002 | Davis et al. | |
| 6,383,748 B1 | 5/2002 | Carpay et al. | |
| 6,692,915 B1 * | 2/2004 | Nallur | 435/6 |

OTHER PUBLICATIONS

Webster's II New Riverside University Dictionary, 1994, p. 875.*

* cited by examiner

*Primary Examiner*—Long V. Le
*Assistant Examiner*—Gary W. Counts
(74) *Attorney, Agent, or Firm*—Amy L. Ressing; John J. Karasek

(57) ABSTRACT

A sensor for a selected analyte in a test sample has (a) a semipermeable membrane with pores for retaining the analyte, where the membrane has been chemically modified by attachment of membrane modifiers; (b) immunoassay labels which have label binding ligands where these label binding ligands will have a binding affinity for the membrane modifiers in the presence of the analyte, and a measurably different binding affinity for the membrane modifiers in the absence of the analyte; and (c) a label detecting system, for detecting the presence of the labels on the membrane.

9 Claims, 3 Drawing Sheets

NANOPOROUS MEMBRANE IMMUNOSENSOR

This is a divisional application of U.S. patent application Ser. No. 09/614,727, inventors Lee et al., filed Jul. 12, 2001, issued as U.S. Pat. No. 6,676,904 on Jan. 13, 2004, the entirety of which is herein incorporated by reference.

BACKGROUND OF THE INVENTION

1. Field of the Invention

The present invention relates generally to assays and more specifically to binding assays, such as antibody/hapten or DNA interactions, using nanoporous membranes for increasing the local concentration of the analyte, to improve the overall sensitivity of the assay. This technique can be used with a wide range of labeling schemes, including radio labeling and labeling with magnetic beads.

2. Description of the Related Art

Binding assays, for example immunoassays, are widely used in the food, medical, and pharmaceutical industries as diagnostic tests for a wide range of target molecules. Many binding assays have been produced and marketed since the principle was first developed.

Immunoassays typically exploit the binding capabilities of antibodies. Antibodies are protein molecules which are frequently considered fighters of infections. They fight infections by binding to the infectious material in a specific manner, forming a complex. This is a signal to the organism to reject that complex. Antibodies may also be produced to specifically bind to a wide range of compounds, as a key fits a lock. However other molecules (e.g., chelators, strands of polynucleic acids, receptors including cellular receptors) that are capable of recognizing and selectively binding other molecules may be employed to detect a wide range of species, such as polynucleic acids (DNA or RNA), polypeptides, glycolipids, hormones, polymers, metal ions, and certain low molecular weight organic species including a number of illegal drugs. To be useful in an assay, this recognition event must generate a signal that is macroscopically observable. The method employed to generate such a signal is one way of distinguishing the various types of immunoassays.

The first immunoassay used radioactive labeling. This radioimmunoassay (RIA) is quite sensitive and widely used, but the hazards, expense, and restrictions associated with handling radioactive material makes alternative immunoassays desirable. Recently, enzyme and fluorescence assays have replaced radioimmunoassays. The present inventors and others have developed techniques using magnetic beads as labels for immunoassays. Other known immunoassay labeling techniques use colloids or fluorescent dyes.

An ongoing goal of immunoassay development is improving the lower limit of detection (LLD). Likewise, it is an ongoing goal of immunoassay development to shorten processing time. This is particularly true in order to counter threats of biological warfare and terrorism, as well as other field applications.

Solid supports are used in many immunoassays, typically as adsorbent layers. Many of these, such as nylon and nitrocellulose membranes have pore sizes greater than 25 nm, to amplify the signal by increasing the surface area of the assay.

Some microbiological assays use membranes to separate and concentrate bacteria. These membranes are typically on the order of 200 nm pore size.

Viruses have been identified with aluminum ultrafiltration membranes with 20 nm pores. Organisms immobilized on these membranes have been identified using both specific and nonspecific dyes.

Chemically selective membranes are used in some chemical sensors to pass the analyte through the membrane. Larger molecules are not allowed to pass through the membrane into the internal sensing solution.

SUMMARY OF THE INVENTION

Accordingly, it is an object of this invention to selectively detect a wide range of target species, with a high degree of sensitivity.

It is a further object of this invention to selectively detect a wide range of target species, with a short processing time.

It is a further goal of this invention to improve sensitivity to 100 to 1000 times that of the current laboratory standard enzyme-linked immunosorbant assay (ELISA), with processing times at least 10 times shorter than ELISA.

These and additional objects of the invention are accomplished by the structures and processes hereinafter described.

An aspect of the present invention is a sensor for a selected analyte in a test sample having (a) a semipermeable membrane with pores for retaining the analyte, where the membrane has been chemically modified by attachment of membrane modifiers; (b) immunoassay labels which have label binding ligands where these label binding ligands will have a binding affinity for the membrane modifiers in the presence of the analyte, and a measurably different binding affinity for the membrane modifiers in the absence of the analyte; and (c) a label detecting system, for detecting the presence of the labels on the membrane.

Another aspect of the invention is a method for detecting an analyte in a test sample, having the steps: (a) modifying a side of a semipermeable membrane, the membrane having pores for retaining the analyte, with membrane modifiers; (b) placing the test sample in contact with the membrane on the side of the membrane with the membrane modifiers; (c) drawing the test sample through the membrane, osmotically or with the application of differential pressure across the membrane, so that any analyte present in the test sample is drawn towards the modified membrane surface; (d) disposing immunoassay labels on the side of the membrane with the membrane modifiers, where these labels have label binding ligands where these label binding ligands will have a binding affinity for the membrane modifiers in the presence of the analyte, and a measurably different binding affinity for the membrane modifiers in the absence of the analyte; and (e) detecting the presence of the immunoassay labels on the membrane.

BRIEF DESCRIPTION OF THE DRAWINGS

A more complete appreciation of the invention will be obtained readily by reference to the following Description of the Preferred Embodiments and the accompanying drawings in which like numerals in different figures represent the same structures or elements, wherein.

DETAILED DESCRIPTION OF THE PREFERRED EMBODIMENTS

Figure 1:
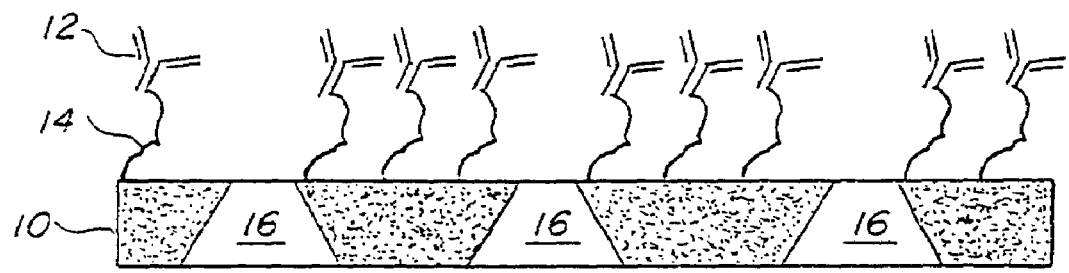
FIG. 1 is a schematic representation of a membrane for a preferred embodiment of the invention.

The following are incorporated by reference herein, in their entireties, for all purposes: (a) U.S. Pat. No. 5,807,758, and (b) Ser. No. 09/008,782.

The term test sample, as used herein, refers to a material suspected of containing the analyte. The test sample can be used directly as obtained from the source or following a pre-treatment to modify the character of the sample. The test sample can be derived from any biological source, such as physiological fluid including, but not intended to be limited to blood, saliva, ocular lens fluid, cerebral spinal fluid, sweat, urine, milk, ascites fluid, mucous, synovial fluid, peritonaeal fluid, amniotic fluid and the like; fermentation broths; cell cultures; chemical reaction mixtures and the like. The test samples can be pretreated prior to use, such as preparing plasma from blood, diluting viscous fluids, and the like. Methods of treatment can involve filtration, distillation, concentration, inactivation of interfering components, and the addition of reagents. In addition to biological or physiological fluids, other liquid samples can be used such as water, food products, aerosol collectors and the like for the performance of environmental or food production assays. In addition, a solid material suspected of containing the analyte can be used as the test sample. In some instances, it may be beneficial to modify a solid test sample to form a liquid medium or to release the analyte.

Binding members, such as the analytes and the membrane and label modifiers of the invention, refers to a member of a binding pair, i.e., two different molecules wherein one of the molecules specifically binds to the second molecule through chemical or physical means. In addition to the well-known antigen and antibody binding pair members, other binding pairs include, but are not intended to be limited to, biotin and avidin, carbohydrates and lectins, complementary nucleotide sequences, complementary peptide sequences, effector and receptor molecules, enzymes cofactors and enzymes, enzyme inhibitors and enzymes, a peptide sequence and an antibody specific for the sequence or the entire protein, polymeric acids and bases, dyes and protein binders, peptides and specific protein binders (e.g., ribonuclease, S-peptide and ribonuclease S-protein), sugar and boronic acid, and similar molecules having an affinity which permits their associations in a binding assay. Furthermore, binding pairs can include members that are analogs of the original binding member, e.g., an analyte-analog or binding member made by recombinant techniques or molecular engineering. If the binding member is an immunoreactant it can be, e.g., an antibody, antigen, hapten, or complex thereof, and if an antibody is used, it can be a monoclonal or polyclonal antibody, a recombinant protein or antibody, a chimeric antibody, a mixture(s) or fragment(s) thereof, as well as a mixture of an antibody and other binding members. The details of the preparations of such antibodies, peptides and nucleotides and their suitability for use as binding members in a binding assay are well-known to those skilled-in-the-art.

The term analyte or analyte of interest, as used herein, refers to the compound or composition to be detected or measured and which has at least one epitope or binding site. The analyte can be any substance for which there exists a naturally occurring binding member or for which a binding member can be prepared. Analytes include, but are not limited to, toxins, organic compounds, proteins, peptides, microorganisms, amino acids, carbohydrates, nucleic acids, hormones, steroids, vitamins, drugs (including those administered for therapeutic purposes as well as those administered for illicit purposes), virus particles and metabolites of or antibodies to any of the above substances. For example, such analytes include, but are not intended to be limited to ferritin; creatinine kinase MIB (CK-MIB); digoxin; phenytoin; phenobarbitol; carbamazepine; vancomycin; gentamycin; theophylline; valproic acid; quinidine; leutinizing hormone (LH); follicle stimulating hormone (FSH); estradiol, progesterone; IgE antibodies; vitamin B2 micro-globulin; glycated hemoglobin (Gly. Hb); cortisol; digitoxin; N-acetylprocainamide (NAPA); procainamide; antibodies to rubella, such as rubella-IgG and rubella-IgM; antibodies to toxoplasmosis, such as toxoplasmosis IgG (Toxo-IgG) and toxoplasmosis IgM (Toxo-IgM); testosterone; salicylates; acetaminophen; hepatitis B virus surface antigen (HBsAg); antibodies to hepatitis B core antigen, such as anti-hepatitis B core antigen IgG and IgM (Anti-HBC); human immune deficiency virus 1 and 2 (HTLV); hepatitis B e antigen (HBeAg); antibodies to hepatitis B e antigen (Anti-Hbe); thyroid stimulating hormone (TSH); thyroxine (T4); total triiodothyronin (Total T3); free triiodiothyronin (Free T3); carcinoembryoic antigen (CEA); and alpha fetal protein (AF); and drugs of abuse and controlled substances, including but not intended to be limited to, amphetamine; methamphetamine; barbituates such as amobarbital, seobarbital, pentobarbital, phenobarbital, and barbital; benzodiazepines such as librium and valium; cannabinoids such as hashish and marijuana; cocaine; fetanyl; LSD; methapualone; opiaets such as heroin, morphine, codine, hydromorphone, hydrocodone, methadone, oxycodone, oxymorphone and opium; phencyclidine; and propoxyhene. The term analyte also includes any antigenic substances, haptens, antibodies, macromolecules and combinations thereof.

Preferably, the pore diameter of the membranes of the present invention is selected to retain the particular analyte of interest. Preferably, the pore diameter of the membranes of the present invention is selected to pass potential interferents that are smaller than the analyte of interest. For some embodiments, it will be preferred that the pore diameter does not exceed 25 nm. For other embodiments, it will be preferred that the pore diameter does not exceed 10 nm. This is sufficient to retain most analytes of interest. For larger analytes of interest, e.g. bacteria, it will be preferred to have pore diameters on the order of about 100 nm, to retain bacteria but to pass viruses. For even larger analytes of interest, e.g. pollen, spores, and dust particles, it will be preferred to have pore diameters on the order of about 1000 nm, to retain these particles but to pass bacteria and viruses.

Referring to FIG. 1, in a preferred embodiment of the invention, a semipermeable membrane 10 has membrane modifiers 12 (typically antibodies) bound to the membrane through linkers 14. These linkers can be chosen from a wide range of linkers used in surface chemistry, but typically will be hydrophillic polymer films. The pores 16 preferably have nominal diameters less than 25 nm.

The membrane modifiers may be the same across the surface of the membrane, or several different types of membrane modifiers may be patterned in an array, to allow for parallel processing within a single test vessel.

Figure 2:
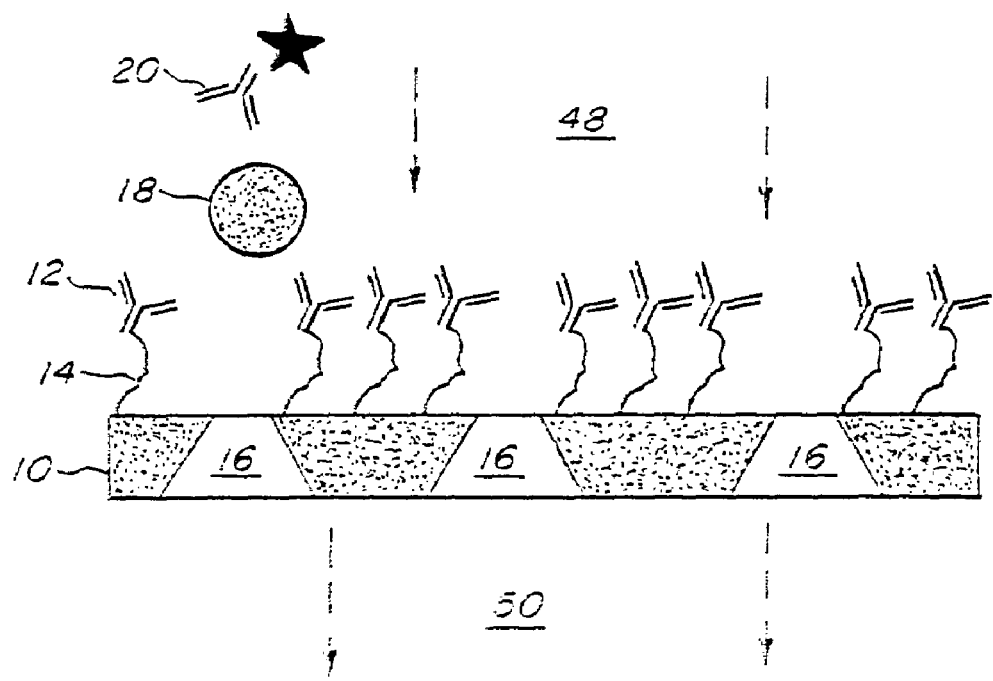
FIG. 2 is a schematic representation of a preferred embodiment of the invention.

Referring to FIG. 2, this membrane may be used to rapidly transport the analyte 18 to the binders if a differential or osmotic pressure is applied across the membrane. This pressure, from a pressure source (not shown) such as a pump, causes bulk flow from a volume on one side of the membrane 48 to a volume on the other side of the membrane 50, as indicated by the dashed arrows. If a differential pressure source is used (as distinct from osmotic pressure), the pressure may be positive or negative. That is, the pump may be configured to increase the pressure on the side of the membrane with the test sample, or to decrease the pressure on the distal side of the membrane. A labeled binder 20 is then used to sense the binding event using a detector (not shown in this figure).

The labeled binders 20 may be the same, or several different types of labeled binders may be patterned used, typically in conjunction with a membrane patterned with several different hmembrane modifiers in an array, to allow for parallel processing within a single test vessel.

Details of alternative assay configurations are described below.

Ultrafiltration Membranes for Sensing

The rate of a chemical reaction at a surface such as a membrane is controlled by at least three phenomena. First, the reactant must be transported to a surface, which is a process that can be controlled by diffusion or convection. If pressure is applied across the membrane, mass transport will be dominated by the convective flow of the sample towards the membrane. The second phenomenon, controlling the overall reaction rate, is the kinetics of the reaction at the interface. In the case of an antibody-antigen interaction, this reaction can be written $$B+A \leftrightharpoons B-A$$

where B is the binder, A is the analyte and B–A is the binder-analyte complex. The amount of bound analyte is determined by the equilibrium constant of the reaction $$K_{eq}=k_1/k_{-1}=[B-A]/[B][A]$$

where $k_1$ and $k_{-1}$ are the forward and reverse rate constants, respectively. The third phenomenon controlling the rate of reaction is the diffusion of the analyte away from the surface. The advantage of using membranes is that if the membrane retains a significant portion of an analyte, the analyte will be rapidly concentrated at the membrane surface resulting in an increase in the amount of analyte bound. Conventional membrane-based immunoassays bind the analyte in their micron size pores producing an active area 1–100 microns deep in the membrane. The ultrafiltration membrane in this invention has a pore size of 25 nm or less, which acts to concentrate the analyte at the surface of the membrane. The observed increase in sensitivity of the assay executed on the ultrafiltration membranes in this invention is attributed to the higher concentration of analyte in the active area of the detector.

Ultrafiltration membranes are widely used for separation and purification processes. The pore size of the membrane, the filtration pressure and the physical properties of the species determine the efficiency of retention of a species. Many of these membranes are composed of organic polymeric materials. Nucleopore membranes, an example of a polymer ultrafiltration membrane, are composed of polycarbonate, have pore sizes of 10–10,000 nm and pore densities of approximately $10^{12}$ m$^{-2}$ (3). Several inorganic ultrafiltration membranes are also available: (i) Anopore® (membranes which are anodically etched from aluminum, have pore sizes ranging from 10–250 nm, and pore density of $10^{12}$–$10^{15}$ m$^{-2}$ (4); (ii) Nanochannel glass membranes are drawn from optical fibers and have similar properties to the Anopore membrane; (iii) Microfabricated membranes currently have larger pore sizes and low density of pores than the Anopore membranes.

For this invention, it is desirable to have an ultrafiltration membrane that has a high density of pores to avoid the need for high differential pressures. In addition, for applications with optical detection it is important that the membrane be flat, optically translucent and not likely to change shape or size during the course of the assay. Organic ultrafiltration membranes do not meet these requirements. The inorganic membranes have the physical properties required for this assay: (i) high flow rates with moderate pressures; (ii) optically translucent membranes that retain their shape when wet; (iii) high retention efficiencies for macromolecules. Studies of 10 nm pore size Anopore membranes at pressures of 100 kPa or less indicate that 6, 20 and 66 percent of 30,000, 67,000 and 150,000 Da proteins are retained, respectively.

Methods of Preparing Activated Membranes

The ultrafiltration membrane in this invention must be functionalized with a binder in order to act as a sensor. However, fouling is a phenomenon that will severely limit the use of ultrafiltration membranes for sensing. Protein fouling has been attributed to adsorption, pore plugging and cake consolidation. We have minimized the effect of protein fouling by executing the immunoassay on a dense hydrophilic polymer film that inhibits protein adsorption. In a preferred embodiment, the active surface of an Anopore membrane was coated with a dense layer of biotinylated poly (ethylene glycol) (PEG) using a polyethylene imine (PEI) adhesion layer (see Example 1). Many variations on this chemistry can be used: (i) The surface can be activated using several different approaches, e.g., silanization or thiolation. (ii) Other hydrophilic polymers could be used to inhibit protein adsorption, e.g., dextran. (iii) Other approaches to inhibit nonspecific protein adsorption are available, e.g., adsorption of proteins such as bovine serum albumin (BSA). The biotin-PEG functionalized membranes have the following advantages: (i) the membranes can be stored in a dry form for extended periods of time; (ii) the concentration of receptors on the membrane can be varied; (iii) the surface can be regenerated. It is especially desirably to make these membranes reusable due to their cost.

Many types of binders can be immobilized on the membrane. Binders against specific analytes may be either directly or indirectly bound to a hydrophilic polymer film. Preferred binders include DNA oligonucleotides, PNA oligonucleotides, polyclonal antibodies and monoclonal antibodies. In a preferred embodiment, antibodies are specifically immobilized on the biotinylated PEG surface using antibody-streptavidin conjugates (see Example 3). Alternatively, binders may be directly bound to the hydrophilic polymeric films functionalized with N-hydroxysuccinimide (NHS), maleimide, or vinyl groups. For example, antibodies can be thiolated with N-succinimidyl S-acetylthioacetate and then reacted with α-vinyl sulfone, ω-n-hydroxysuccinimide PEG, 3,000 MW functionalized polymers. There are of course many variations on this chemistry.

Assay Methods

The assay method will be composed of at least three steps: (i) preparation of the sample, (ii) reaction of the analyte at the membrane surface and (iii) detection of the binding events.

Those skilled in the art will recognize that complex samples may require pre-purification and/or cellular disruption of bacteria. For example, we have found that immunoassays involving bacteria have superior sensitivity if the bacteria are disrupted using either chemical or mechanical means. In the preferred embodiment all samples would be exposed to ultrasonic power in the presence of inorganic particles (See Example 4 below).

Those skilled in the art will realize that there are numerous configurations in which the analyte can be bound and detected. Three examples are described in schemes 1–3.

| Scheme 1: Direct Sandwich | |
|---|---|
| Capture membrane | Complex |
| Membrane-binder | analyte - binder-label |
| Membrane-biotin | streptavidin-binder - analyte - binder-label |

This assay can be executed in a series of sequential steps on the membrane or the complex could be formed in solution and then bound on the membrane. Note that convective transport may be used at each step of the assay to enhance the response time.

| Scheme 2: Indirect Sandwich | |
|---|---|
| Capture membrane | Complex |
| Membrane-binder | analyte - binder - antibinder-binder-label |
| Membrane-biotin | streptavidin-binder - analyte - antibinder-binder-label |

In this case, it would probably be most convenient to execute the assay on the membrane. Again, convective transport may be used at each step of the assay to enhance the response time.

Scheme 3: Competitive

In some instances the analyte might have only one epitope available for binding. In this case a competitive assay may be used to detect the analyte. Labeled analyte would be added to the sample and its differential binding would be detected.

In these assay configurations the label is used to produce a signal that is related to the amount of analyte in the sample. The signal producing system can be composed of one or more members. The measurement of this signal will normally involve electromagnetic radiation absorption or emission. The signal producing systems can be any suitable sytem, including chromogens, catalyzed reactions, chemiluminesence, and radioactive labels. In the preferred embodiment the force differentiation assay will be used to detect the analyte, see Example 2.

Apparatus

The assay apparatus will be composed of a membrane, fluid handling system, and detector. A fluid handling system and detector are described in this section.

The differential pressure necessary to transport the analyte to the membrane surface may be produced osmotically, or with either positive pressure or negative pressure from a pump. In cases in which the sample will be handled batch wise conventional vacuum filtration equipment or a syringe filtration apparatus may be used (see examples).

Figure 3:
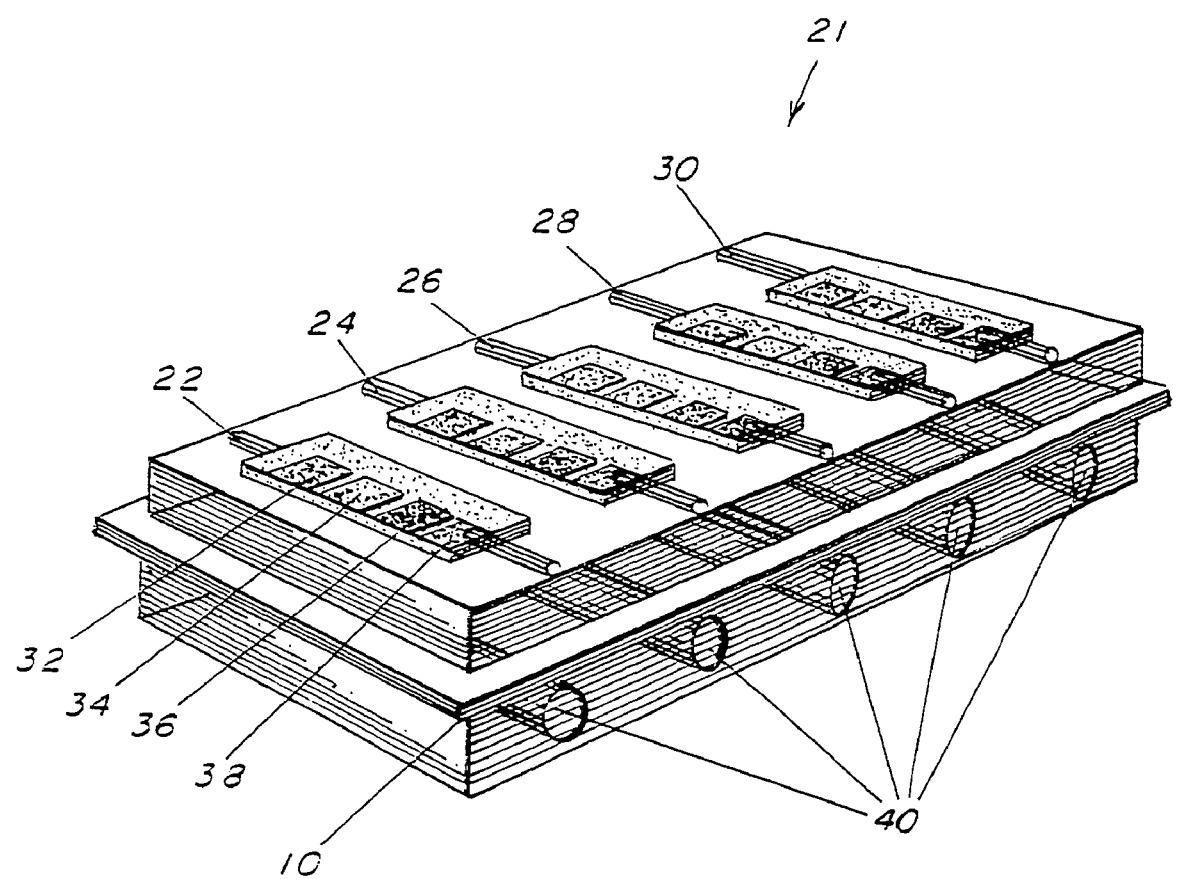
FIG. 3 is a schematic representation of a fluid handling system for a preferred embodiment of the invention.

Biosensors typically require automated processing and continuous operation. A schematic of a cell for performing continuous assays is shown in FIG. 3. This 1×0.25×0.5" 21 cell is drawn with five reaction chambers 22, 24, 26, 28, 30 in which the sample passes from left to right. This cell makes it possible to run five sequential assays if each surface used one time. If the surfaces can be regenerated, numerous assays can be run in a single cell. In this cell the active area of each chamber is patterned with four binders 32, 34, 36, 38. Patterning a surface with binders has the advantage that multiple analytes can be detected while simultaneously running internal standards. Techniques for patterning binders on solid surface are well known to those skilled in the art. A preferred embodiment would be to use ink jet technology to accurately distribute small volumes of binder-streptavidin conjugates on specific areas of biotin-PEG functionalized membrane 10. This cell includes a manifold 40 that will allow the sample to be channeled to the active area of the membrane and pass through the cell. Clearly, this is not the only geometry in which this cell could be constructed.

Labeling Techniques

As noted above, the labeling system can be any suitable system for labeling in immunoassays. Suitable systems include those using labels such as chromogens, catalyzed reactions, chemiluminesence, radioactive labels, and magnetic beads. In a preferred embodiment the force differentiation assay (Ser. No. 09/008,782) will be used to detect the analyte.

Chromogens

Chromogens include compounds which absorb light in a distinctive range, so that a color may be observed, or emit light when irradiated with light of a particular wavelength or wavelength range e.g. fluorescers.

Colloidal particles such as nanometer scale gold are excellent chromogens. Further, magnetic-polymer composites will also adsorb light.

The choice of dye may be varied widely, being primarily chosen to provide an intense color with minimum absorption by the immunosorbing zone support. Illustrative dye types include quinoline dyes, triarylmethane dyes, acridine dyes, alizarin dyes; phthaleins, insect dyes, azo dyes, anthraquinoid dyes, cyanine dyes, phenazathionium dyes, and phenazoxonium dyes.

A wide variety of fluorescers may be employed either by themselves or in conjunction with quencher molecules. Fluorescers of interest fall into a variety of categories having certain primary functionalities. These primary functionalities include 1- and 2-aminoaphthalene, p,p'-diaminostilbenes, pyrenes, quaternary phenanthridine salts, 9-aminoacridines, p,p'-diaminobenzophenone imines, anthracenes, oxacarbocyanine, merocyanine, 3-aminoequilenin, perylene, bis-benzoxazole, bis-p-oxazolyl benzene, 1,2-benzophenazin, retinol, bis-3-aminopyridinium salts, hellebrigenin, tetracycline, sterophenol, benzimidazolylphenylamine, 2-oxo-3-chromen, indole, xanthene, 7-hydroxycoumarin, phenoxazine, salicylate, strophanthidin, porphyrins, triarylmethanes and flavin.

Individual fluorescent compounds which have functionalities for linking or can be modified to incorporate such functionalities include dansyl chloride, fluoresceins such as 3,6-dihydroxy-9-phenylxanthhydrol, rhodamineisothiocyanate, N-phenyl 1-amino-8-sulfonatonaphthalene, N-phenyl 2-amino-6-sulfonatonaphthalene, 4-acetamido-4-isothiocyanatostilbene-2,2'-disulfonic acid, pyrene-3-sulfonic acid, 2-toluidinonaphthalene-6-sulfonate, N-phenyl, N-methyl 2-aminonaphthalene-6-sulfonate, ethidium bromide, atebrine, auromine-0, 2-(9'-anthroyl)palmitate, dansyl phosphatidylethanolarmine, N,N'-dioctadecyl oxacarbocyanine, N,N'-dihexyl oxacarbocyanine, merocyanine, 4-(3'-pyrenyl)

butyrate, d-3-aminodesoxyequilenin, 12-(9'-anthroyl)stearate, 2-methylanthracene, 9-vinylanthracene, 2,2'-(vinylene-p-phenylene)-bis-benzoxazole, p-bis[2-(4-methyl-5-phenyloxazolyl)]benzene, 6-dimethylamino-1,2-benzophenazin, retinol, bis(3'-aminopyridinium) 1,10-decandiyl diiodide, sulfonaphthylhydrazone of hellebrigenin, chlortetra-cycline, N-(7-dimethylamino-4-methyl-2-oxo-3-chromenyl) maleimide, N-[p-(2-benzimidazolyl)-phenyl]maleimide, N-(4-fluoranthyl) maleimide, bis (homovanillic acid), resazarin,4-chloro-7-nitro-2.1.3-benzooxadiazole, merocyanine 540, resorufin, rose bengal, and 2,4-diphenyl-3(2H)-furanone.

Fluorescers are preferred to absorptive dyes to the extent that a single fluorescer can provide for multiplication of a signal. By irradiating a fluorescer with light, one can obtain a plurality of emissions. Thus, a single label can provide for a plurality of measurable events.

Various other combinations and protocols could be employed depending upon the nature of the analyte.

Catalysis

Both enzymatic and nonenzymatic catalysts may be employed. Preferably, enzymatic catalysts will be employed, since they frequently provide for more rapid reactions, a desirable versatility in the variety of reactions, and have well characterized properties.

In choosing an enzyme, there will be many considerations in addition to those involved with the reaction of interest. These considerations include the stability of the enzyme, the desirability of a high turnover rate, the sensitivity of the rate to variations in the physical environment, the nature of the substrate(s) and product(s), the availability of the enzyme, the effect of conjugation of the enzyme on the enzyme's properties.

Of particular interest in the subject invention is the use of coupled catalysts, usually two or more enzymes, where the product of one enzyme serves as the substrate of the other enzyme. One or more enzymes are bound to the surface, while one enzyme is always bound to a mip. Alternatively, two enzymes can be bound to a mip and an additional enzyme may be bound to the surface.

The solute will be the substrate of any one of the enzymes, but preferably of an enzyme bound to the surface. The enzymatic reaction may involve modifying the solute to a product which is the substrate of another enzyme or production of a compound which does not include a substantial portion of the solute, which serves as an enzyme substrate. The first situation may be illustrated by glucose-6-phosphate being catalytically hydrolyzed by alkaline phosphatase to glucose, wherein glucose is a substrate for glucose oxidase. The second situation may be illustrated by glucose formed from glucose-6-phosphate being oxidized by glucose oxidase to provide hydrogen peroxide which would enzymatically react with the signal generator precursor and a peroxide to produce the signal generator.

Coupled catalysts can also involve an enzyme with a non-enzymatic catalyst. The enzyme can produce a reactant which undergoes a reaction catalyzed by the non-enzymatic catalyst or the non-enzymatic catalyst may produce a substrate (includes coenzymes) for the enzyme. For example, G6PDH could catalyze the conversion of NAD and G6P to NADH which reacts with tetrazolium salts to produce an insoluble dye.

A wide variety of nonenzymatic catalysts which may be employed in this invention are found in U.S. Pat. No. 4,160,645, the appropriate portions of which are incorporated herein by reference. The nonenzymatic catalysts employ as reactants a first compound which reacts by a 1-electron transfer and a second compound which reacts by a 2-electron transfer, where the two reactants are capable of reacting with each other slowly, if at all, in the absence of the catalyst.

Various combinations of enzymes may be employed to provide a signal generating compound at the surface. Particularly, combinations of hydrolases may be employed to produce an insoluble signal generator. A single hydrolase may act in a substantially equivalent manner to an enzyme pair by employing the appropriate substrate. Alternatively, combinations of hydrolases and oxidoreductases can provide the signal generator. Also, combinations of oxidoreductases may be used to produce an insoluble signal generator. Usually there will be a preferred catalyst at the surface, since as indicated previously, by appropriate choice of the catalyst at the surface, a greater number of reagents may be combined in a single formulation.

Chemiluminescers

An alternative source of light as a detectible signal is a chemiluminescent source. The chemiluminescent source involves a compound which becomes electronically excited by a chemical reaction and may then emit light which serves as the detectible signal or donates energy to a fluorescent acceptor.

A diverse number of families of compounds have been found to provide chemiluminescence under a variety of conditions. One family of compounds is 2,3-dihydro-1,-4-phthalazinedione. The most popular compound is luminol, which is the 5-amino compound. Other members of the family include the 5-amino-6,7,8-trimethoxy- and the dimethylamino[ca]benz analog. These compounds can be made to luminesce with alkaline hydrogen peroxide or calcium hypochlorite and base. Another family of compounds is the 2,4,5-triphenylimidazoles, with lophine as the common name for the parent product. Chemiluminescent analogs include para-dimethylamino and -methoxy substituents. Chemiluminescence may also be obtained with oxalates, usually oxalyl active esters e.g. p-nitrophenyl and a peroxide e.g. hydrogen peroxide, under basic conditions. Alternatively, luciferins may be used in conjunction with luciferase or lucigenins.

Radioactive Levels

Various radioisotope find common use. These include tritium ($^3H$), radioactive iodine ($^{125}I$), radioactive carbon ($^{14}C$), radioactive phosphorus ($^{32}P$); or the like. Methods for labeling of compounds with radioactive labels are well known in the art.

Magnetic Bead Labeling

Magnetic beads can be used as labels for immunoassays. U.S. Pat. No. 5,807,758 describes one method of using magnetic beads as labels, where modified beads will selectively bind to a modified cantilever, depending on whether the analyte is present. An applied magnetic field will exert a force on the cantilever, which may be detected using conventional techniques for measuring cantilever deflection.

Preferably, the force differentiation assay, described in co-pending application Ser. No. 09/008,782, is used. In this technique, the membrane and the magnetic beads are modified with specific binding agents, so that these bead modifiers will have a binding affinity for the membrane modifiers in the presence of the analyte species, and a measurably different binding affinity for the membrane modifiers in the absence of the analyte species. The beads and the test sample are introduced into the test vessel, and an adjustable magnetic field source is used to apply a magnetic force to the beads. An imaging system is used to determine whether the beads are bound to the membrane, thereby testing for the analyte.

Figure 4:
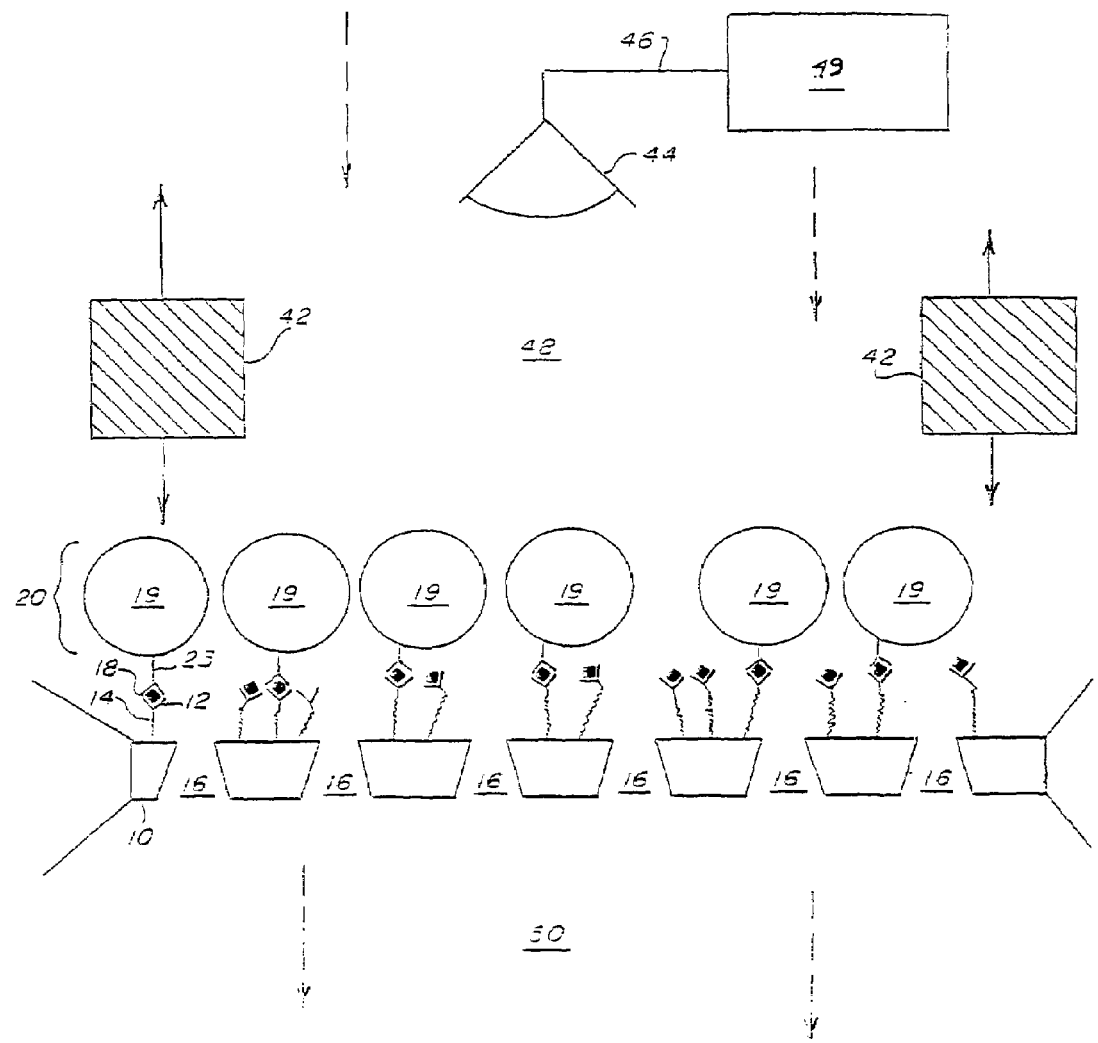
FIG. 4 is a schematic representation of a preferred embodiment of the invention using the force differentiation assay as the labeling and detection technique.

Referring to FIG. 4, depicting a sandwich assay configuration for the present invention, a nanoporous membrane 10 is disposed in a test vessel, dividing the test vessel into two volumes 48, 50. Magnetic beads 19 are disposed in the vessel, within the first volume 48.

The beads 19 are modified with molecules which are referred to herein as bead modifiers 23, and the membrane 10 is modified on the side facing the first volume with membrane modifiers 12. Both of these types of modifiers will be selected from those molecules that are capable of recognizing and selectively binding other molecules, including antibodies, haptens, polynucleic acids, polypeptides, glycolipids, hormones, polymers, metal ions, and certain low molecular weight organic species (see above).

The mechanism for applying a variable, normal magnetic field to the beads 19 is shown here as a movable annular magnet 42. The annular magnet produces a uniform $\vec{B}$ field which is oriented along its axis across millimeter size areas. It has been discovered that a millimeter scale NdFeB magnet can apply a uniform field over sample areas consistent with imaging by optical microscopy, if the magnet is carefully centered. This normal B field acts upon the bead 10 to create a normal force (F) on the beads 19, which in turn puts tension on the bond between the bead 19 and the membrane 10. Since covalent bonds are typically much stronger than specific molecular interactions (such as antibody-hapten interactions), the strength of the linkage between the bead and the membrane is limited by the strength of this specific molecular interaction.

In addition to annular magnets, other magnetic geometries may be used, such as discs, bars, or other flat shapes, so long as the B field has the desired properties in the area under observation. High permeability focusing cones positioned between the magnet and the substrate may be used to shape the field so that the field has a higher-gradient. Since the force on a paramagnetic bead is related to the field gradient, the use of these cones will tend to increase the forces acting on the beads.

As the field intensity is varied, eventually a point is reached where the bead separates from the substrate, indicating that the force from the field has exceeded the strength of nonspecific or specific molecular interaction. By observing when beads separate from the substrate, one can observe when this point is reached. It should be noted that this separation point will depend not only on the force applied to the linkage between the bead and the substrate, but also on the observation time and the system temperature.

A preferred embodiment of the invention further comprises a microscope, typically an optical microscope 44, for imaging beads bound to the substrate, and separated from the substrate. Preferably, the microscope 44 is connected through connecting electronics (often including a video camera) 46 to a computer 48 or to a video recorder for analyzing images from the microscope. The advantage of the annular magnet 42 is that it does not interfere with transmitted light in an optical microscope. However, reflected light microscopy makes it possible to use solid magnet geometries.

For this preferred embodiment of the invention, it will be important to have the capacity to identify single beads (as distinguished from aggregates), to count the beads quickly and reliably, and to determine their relative position on the substrate. This positional information is advantageous for several reasons. For example, in some applications it may be advantageous to pattern the substrate by attaching different types of substrate modifiers on different regions of the substrate. It will be advantageous in such applications to identify where on a substrate a given bead is bound. Accordingly, the imaging system for the present invention, including the microscope 44, computer 48, and connecting electronics 46, should have the capacity to count beads that have separated from the substrate (or, alternatively, count beads that have not separated from the substrate). Typically, this will mean capturing a digital image from the microscope (either directly using a frame grabber or indirectly using a video recorder) and analyzing it using image analysis algorithms on the computer 48.

Additionally, the imaging system for the present invention preferably has the capacity to discriminate between single beads on the substrate and clusters of two or more beads on the substrate, based on their size. It has been discovered that non-uniform surface chemistries and magnetic fields of the structures taught by Rohr produce the following non-ideal behavior.

Brownian motion causes the beads to move on the surface. This motion leads a significant fraction of the beads to form dimers and aggregates, if the beads are "sticky" (i.e., tend to stay together once they are brought together). Multibody interactions in these aggregates lead to enhanced magnetization of the clusters when the $\vec{B}$ field is applied, and greatly accelerates their displacement. Image analysis allows one to identify the level of aggregation and correct for its effects. It should be noted that the fraction of beads as monomers and aggregates is strongly related to the amount of analyte on the surface and the nonspecific adhesive properties of the surfaces; therefore, aggregation can also be used to independently determine analyte concentration and surface properties.

Furthermore, under all but the most ideal circumstances a fraction (2–20%) of the beads adhere to the surface non-specifically, even under high forces (>2 pN). It has been observed that these beads capture other beads that move laterally in the solution, and thus form string shaped aggregates. Image analysis makes it possible to identify these aggregates and discard them from consideration. Detection techniques that measure integrated signals can not distinguish these beads from specifically bound beads.

Nonspecific adhesion between beads, and between beads and the membrane, appears to increase when the beads are loaded with proteins, which suggests protein-protein interactions are the primary source for this adhesion.

It has been discovered that a commercially available microscope (Axiovert 100 microscope with a 63×Acroplan objective, Carl Zeiss, One Zeiss Dr., Thornwood, N.Y. 10594), electronics (VE-1000 CCD72 black/white video system from DAGE-MTI, Michigan City, Ind.; DT 3152 Fidelity PCI frame grabber, Data Translation, 100 Locke Dr, Marlboro, Mass. 01752-1192), image analysis software (Image-Pro Version 2.0, Media Cybernetics, 8484 Georgia Ave., Silver Spring, Md. 20910), and computer (Pentium 66 MHz Computer with 1 GB hard drive) will reliably identify superparamagnetic 2.6 micron diameter beads and clusters thereof. Once clusters have been identified, they can be ignored, i.e. discounted from further analysis. Thus, when the position of the beads is monitored (i.e., monitored for whether the beads are bound or unbound to the substrate), only single beads will be analyzed, dramatically improving the accuracy of the detector.

It has further been discovered that beads imaged through such a microscope may be monitored for movement, and that unbound beads will move over short time scales, a fraction of a second or a few seconds, permitting these beads to be identified as unbound, and likewise discounted from further analysis.

The magnitude of the adhesive force between the bead and surface is determined by several factors, i.e., the magnitude of the nonspecific forces, the number of specific molecular interactions linking the bead to the surface and the manner in which these interactions are stressed.

Surface modification chemistries (described below) have been developed that consistently produce very low nonspecific adhesive forces in a majority of beads. Typically, 80–98% of the beads can be removed from a surface at force equivalent to their buoyant weight, i.e., ≈40 femtoNewtons (fN) in the case of Dynal's M280 beads. The number of specific molecular interactions linking a bead to the surface will depend on the density and flexibility of ligands and receptors on the bead and surface.

EXAMPLES

Having described the invention, the following examples are given to illustrate specific applications of the invention, including the best mode now known to perform the invention. These specific examples are not intended to limit the scope of the invention described in this application.

Example 1

Preparation of Functionalized Membrane: PEG Biotin Membrane with Streptavidin-Antibody Conjugate.

Anodisc membrane was hydrated with 200 ml of pure water for 1 minute. Excess water was removed, and the membrane was rinsed with 50 mM sodium bicarbonate buffer ($NaHCO_3$) pH 8.2. Excess buffer was removed from themembrane and 5% (w/v) PEI in 50 mM sodium bicarbonate buffer ($NaHCO_3$) pH 8.2 was added. Incubation was at room temperature for 1 hour.

The membrane was rinsed three times with water and once with 50 mM sodium bicarbonate buffer ($NaHCO_3$) pH 8.2. Excess liquid was removed from the membrane, followed by the addition of a-biotin, w-NHS poly(ethylene glycol)-carbonate, MW 3,400 (Shearwater Polymers, Huntsville, AL) at 20 mg/mL in 50 mM sodium bicarbonate buffer ($NaHCO_3$) pH 8.2. The PEG was incubated at room temperature for 2 hours, excess PEG-biotin solution was washed off with three rinses of water and stored dry.

A sandwich immunoassay was built on the PEG-biotin functionalized Anodisc membranes. The membranes were rehydrated with 200 ml of water for 1 minute and rinsed with 0.1 M phosphate buffered saline (PBS) pH 7.4. Next 1% (w/v) bovine serum albumin (BSA) (Sigma Chemical Company, St. Louis, Mo.) was added to the surface for 1 hour to block non-specific sites. The membrane was then washed 3 times using PBS with 0.05% Tween 20 (PBST). Next, the appropriate antibody-streptavidin conjugates were diluted in PBST and added to the membrane in 200 ml volumes. The optimal conjugate concentration was determined by serial dilution analysis. Rabbit antibody-streptavidin for *B. globigii* and Goat antibody-streptavidin for ovalbumin and MS-2 were used as the capture antibodies. The conjugates were incubated on the surface for 1 hour, then excess antibodies were removed by washing 3 times using PBST and rinsing once with PBS. The surfaces can be stored in PBS at 4 C for up to 12 hrs.

Example 2

Ovalbumin (OVA) Assay

A functionalized membrane was incubated with the appropriate dilution of goat antibody-(ovalbumin)-streptavidin conjugate (200 ml) and then washed with PBST to remove unbound antibodies as described in Example 1.

The membrane was then placed into a glass microanalysis vacuum membrane holder (Fisher Scientific, Springfield, N.J.) composed of a borosilicate glass funnel, base, fritted glass support, spring clamp, and No. 5 stopper. A 1 mL sample of a standard solution of known concentration (analytes=Ova ng/ml=0, 10, 1, 0.1, 0.01) was added to the filtration holder and incubated for 5–10 minutes. The analyte solution was then filtered using a water aspirator for 5 minutes. Unbound analyte was removed by washing the membrane 3 times with PBST. A sandwiching antibody, rabbit-antibody-ovalbumin (affinity purified), was then added to the membrane (200 μl) at 2 μg/ml in PBST and incubated for 1 hour. The more ovalbumin present in the test solution the more $2^{nd}$ antibody will bind. The membrane was then washed three times with PBST, and rinsed with PBS. The membrane was then placed onto a glass microscope slide, excess fluid was removed, and anti-rabbit IgG-Seramag beads diluted in 0.1% (w/v) BSA were added to the membrane and incubated for 30 minutes.

The samples were analyzed using a Carl Zeiss Axiovert 100 TV inverted microscope fitted with a motorized stage (Ludl Electronics, N.Y.). A custom written software program operated the reader, this enabled computer control of hardware via a serial port. The image analysis was performed in real time by accessing routines provided by Image Pro plus, version 3.0 commercial imaging software (Media Cybernetics). The membrane was analyzed in 3 positions consisting of a 128×96 mm area at a distance of 200 μm apart using a water immersion objective (63×), 0.9 numerical aperture (NA) (Carl Zeiss) before and after exposure to the magnet. A magnetic force, was applied using a NdFeB block magnet (Magnet Sales and Mfg. Co., Culvert City, Calif.) magnetized perpendicular to the substrate. The magnet was placed 0.1 mm from the surface for 10 seconds to remove unbound beads from the sample surface. The remaining beads were then counted.

The standard curve was constructed from these data and was expressed as the percentage of beads bound to the surface after exposure to the magnetic force versus concentration of the analyte. The cut off values to determine whether a sample was positive or negative was calculated by taking the percent bound beads of the negative control, PBST solution, plus three standard deviations. The average binding for the various analytes are as follows (ng Ovalbumin): 1 ng=81%, 0.1 ng=41%, 0.01 ng=26%, 0.001 ng=1%, 0 ng=2%. The results show a sensitivity of 0.01 ng for Ovalbumin.

Example 3

MS-2 Assay

A functionalized membrane was incubated with the capture antibody, goat antibody-(MS-2)-streptavidin conjugate, and rinsed with PBST as stated in Example 1. Follow the same procedure as stated in Example 2 with these few exceptions: capture antibody used was goat antibody-(MS-2)-streptavidin conjugate; analytes=MS-2=0, $10^5$, $10^4$, $10^3$ pfu/ml; sandwiching antibody, Rabbit-antibody-MS-2, was then added to the membrane (200 µl) at 1 µg/ml in PBST. The average binding for the various analytes are as follows (pfu MS2): 0=4%, $10^5$=66.5%, $10^4$=35.4%, $10^3$=22% The results show a sensitivity for MS-2 exceeding $10^3$ pfu/ml.

Example 4

*Bacillus globigii* (BG) Assay

As previously noted, cellular disruption of bacteria, via chemical or mechanical means is preferred before the sample can be added to the reaction chamber. These methods include subjecting the bacterial cells to a hot detergent treatment, freeze-thaw cycles, bead mill-homogenization, or a commercially available bacterial protein extraction reagent (B-PER, Pierce). Since *B. globigii* is a spore forming bacteria, the most effective method of cell disruption is bead mill homogenization (18).

A functionalized membrane was incubated with Rabbit antibody-(BG)-streptavidin conjugate and rinsed with PBST. In order to break apart *B. globigii*, the sample was first subjected to bead mill homogenization (18). Glass beads (0.1–1 mm) were added to a 0.75 ml BG solution: 1 g glass beads per microcentrifuge tube. The sample was added to the bead beater (Mini-Bead Beater-8, Bio-Spec products) and mixed on "Homogenize" for 3 minutes. The samples were then centrifuged at 12,000×g for 6 minutes. The supernatant was then removed and recentrifuged for 2 minutes at 12,000×g to eliminate any extraneous glass particles.

A novel method of cellular disruption involving glass beads was also used. The analyte solution was added to 1 g of glass beads (0.1–1 mm) in a borosilicate glass culture tube and sonicated using a Branson Sonifier (Branson Ultrasonics Corporation, Danbury Conn.) for 3 minutes. The supernatant was removed and added to a microcentrifuge tube and centrifuged at 12,000×g for 6 minutes.

1 ml of supernatant was removed and added to the filtration apparatus for incubation with the functionalized surface (analytes=BG=0, $10^5$, $10^4$, $10^3$, $10^{2.5}$ cfu/ml) for 5–10 minutes and then filtered using a water aspirator for 5 minutes. Unbound analyte was removed by washing the membrane 3 times with PBST, then a sandwiching antibody, goat-antibody—*B. globigii*, was added to the membrane (200 µl) at 2 µg/ml in PBST and incubated for 1 hour. The more *B. globigii* present in the test solution the more $2^{nd}$ antibody will bind. The membrane was then washed three times with PBST, and rinsed with PBS.

The membrane was then placed on a glass microscope slide, excess fluid was removed, and anti-goat IgG-Seramag beads diluted in 0.1% (w/v) BSA were added to the membrane and incubated for 30 minutes. The analysis of the samples was the same as in Example 2. The average binding for the various analytes are as follows (cfu *B. globigii*): 0=14%, $10^5$=93%, $10^4$=85%, $10^3$=66%, $10^{2.5}$=44%. The sensitivity for *B. globigii* exceeding $10^{2.5}$ cfu/ml Example 5

Ova in Presence of MS-2

A functionalized membrane was incubated with goat antibody—(ovalbumin)—streptavidin conjugate and rinsed with PBST as described in Example 1. The same procedure as stated in example 2 was followed with these few exceptions: Capture antibody was goat antibody-(ovalbumin)-streptavidin conjugate; analytes=Ova ng/ml=0, 10, 1, 0.1, 0.01, Ova 1 ng/ml+MS-2 $10^8$ pfu/ml, Ova 1 ng/ml+MS-2 $10^5$ pfu/ml, Ova 0.01 ng/ml+MS-2 $10^8$ pfu/ml, Ova 0.01 ng/ml+MS-2 $10^8$ pfu/ml; the sandwiching antibody, rabbit-antibody-ovalbumin (affinity purified), added was at 2 µg/ml in PBST. The membrane was then washed three times with PBST, and rinsed with PBS.

The membrane was then placed on a glass microscope slide, excess fluid was removed, and anti-rabbit IgG-Seramag beads diluted in 0.1% (w/v) BSA were added to the membrane and incubated for 30 minutes. The results show a sensitivity of 0.01 ng for Ovalbumin. The total binding decreases by 32% in the Ova 1 ng/ml+MS-2 $10^8$ pfu/ml and the remainder of the mixed analyte assays show a decrease of 10% in binding. This is most likely caused by steric hindrance.

Example 6

OVA Assay-with Filtration of $2^{nd}$ Antibody

A functionalized membrane was incubated with goat antibody—(ovalbumin)—streptavidin conjugate and rinsed with PBST as described in example 1. The membrane was then placed into the glass microfilter holder and a 1 mL sample (analytes=Ova ng/ml=0, 10, 1, 0.1, 0.01) was added to the filtration holder and incubated for 5–10 minutes. The analyte solution was then filtered using a water aspirator for 5 minutes. Immediately following filtration of the analyte, the sandwiching antibody, rabbit-antibody-ovalbumin (affinity purified), was then added to the membrane at 1 µg (0.5 µg/ml over a 2 ml volume). The secondary antibody was passed through the membrane slowly to concentrate the antibody at the interface. The membrane was then washed three times with PBST, and rinsed with PBS. The membrane was then placed on a glass microscope slide, excess fluid was removed, and anti-rabbit IgG-Seramag beads diluted in 0.1% (w/v) BSA were added to the membrane and incubated for 30 minutes. The membrane was analyzed as described in Example 2. The results were as follows (ng Ovalbumin): 0=15%; 1=81%; 0.01=55%. The sensitivity of the Ovalbumin assay with filtration of $2^{nd}$ antibody was 0.01 ng.

Obviously, many modifications and variations of the present invention are possible in light of the above teachings. It is therefore to be understood that, within the scope of the appended claims, the invention may be practiced otherwise than as specifically described.

What is claimed is:

1. A method for detecting a selected analyte in test solution, comprising providing a sensor comprising:

a test vessel;

a semipermeable membrane having pores for retaining the analyte, wherein said semipermeable membrane divides said test vessel into a first volume and a second volume, wherein said pores are selected to prevent the analyte from passing into or through said membrane, wherein said membrane is chemically modified by attachment of membrane surface modifiers on at least a side facing said first volume but not within said pores, wherein said membrane supports a 100 kPa pressure load, said membrane is functionalized with a binder at the surface of said membrane in order for said membrane to act as a sensor;

assay labels, disposed within said first volume, said assay labels having label modifiers, said label modifiers having a binding affinity for the membrane modifiers in the presence of the analyte, and a measurably different binding affinity for said membrane modifiers in the absence of analyte;

a pressure source, for driving said test solution from said first volume into said second volume through said modified surface of said membrane contacting the test solution with said membrane and;

removing labels not bound to said analyte and;

detecting the presence or absence of said analyte by detecting the presence or absence of said labels on said membrane.

2. The method of claim 1 wherein said membrane has pores not greater than 10 nm in diameter.

3. The method of claim 1, wherein said membrane has a pore density of at least $10^{15}/m^2$.

4. The method of claim 1, wherein said membrane is essentially flat and optically translucent when wet.

5. The method of claim 4, wherein said membrane remains translucent, and the shape of said membrane remains flat even under pressure associated with flow of solution through said membrane.

6. The method of claim 1, wherein said membrane is an aluminum oxide membrane.

7. The method of claim 1, wherein said modified side of said membrane is modified with a biotin-polyethyleneglycol (PEG) using a polyethyleneimine (PEI) layer.

8. The method of claim 1 wherein said pores allow a solvent to pass through while preventing flow of said binder, analyte, or assay labels.

9. The method of claim 1, wherein said membrane has pores not greater than 20 nm in diameter.

* * * * *